(12) United States Patent
Wasson, Jr. et al.

(10) Patent No.: US 9,795,346 B2
(45) Date of Patent: Oct. 24, 2017

(54) RADIATION SHIELD ASSEMBLY

(71) Applicant: Trans-Radial Solutions LLC, Roebuck, SC (US)

(72) Inventors: Barney C. Wasson, Jr., Grey Court, SC (US); Andrew W. Shealy, Roebuck, SC (US); James E. Conner, Landrum, SC (US)

(73) Assignee: Trans-Radial Solutions LLC, Roebuck, SC (US)

( * ) Notice: Subject to any disclaimer, the term of this patent is extended or adjusted under 35 U.S.C. 154(b) by 0 days.

(21) Appl. No.: 15/309,897

(22) PCT Filed: Aug. 14, 2015

(86) PCT No.: PCT/US2015/045180
§ 371 (c)(1),
(2) Date: Nov. 9, 2016

(87) PCT Pub. No.: WO2016/086455
PCT Pub. Date: Jun. 9, 2016

(65) Prior Publication Data
US 2017/0265824 A1    Sep. 21, 2017

Related U.S. Application Data (60) Provisional application No. 62/087,282, filed on Dec. 4, 2014.

(51) Int. Cl.
*A61B 6/10*    (2006.01)
*A61B 6/00*    (2006.01)

(52) U.S. Cl.
CPC .............. *A61B 6/107* (2013.01); *A61B 6/487* (2013.01)

(58) Field of Classification Search
CPC ................................ A61B 6/107; A61B 6/487
USPC ........................................................ 250/515.1
See application file for complete search history.

(56) References Cited

U.S. PATENT DOCUMENTS

| | | |
|---|---|---|
| 3,967,128 A | 6/1976 | Smulewicz |
| 3,984,695 A | 10/1976 | Collica |
| 3,984,696 A | 10/1976 | Collica |
| 4,255,667 A | 3/1981 | Bolin et al. |
| 4,662,366 A | 5/1987 | Tari |
| 4,742,981 A | 5/1988 | Converse |
| 4,893,323 A | 1/1990 | Cook, III |
| 4,957,120 A | 9/1990 | Grier-Idris |
| 4,970,900 A | 11/1990 | Shepherd et al. |
| 5,006,718 A | 4/1991 | Lenhart |

(Continued)

FOREIGN PATENT DOCUMENTS

| | | |
|---|---|---|
| GB | 2011/2472246 A1 | 2/2011 |
| WO | 2002/015198 A1 | 2/2002 |

(Continued)

OTHER PUBLICATIONS

Bertrand, Olivier et al. "Best Practices for Transradial Approach in Diagnostic Angiography and Intervention," Wolters Kluwer Health, pp. 272-273 (2015).

*Primary Examiner* — Nicole Ippolito
*Assistant Examiner* — Hanway Chang
(74) *Attorney, Agent, or Firm* — Thrive IP; Bernard S. Klosowski (57) ABSTRACT

Systems and methods for providing a radiopaque shield affixed to a medical device hangar. Such systems and methods reduce radiation exposure to circulating medical staff during fluoroscopy procedures and reduce equipment clutter and cost.

25 Claims, 7 Drawing Sheets

(56) References Cited

U.S. PATENT DOCUMENTS

| | | |
|---|---|---|
| 5,742,962 A | 4/1998 | Yoshino |
| 6,101,650 A | 8/2000 | Omdal |
| 6,467,487 B1 | 10/2002 | Rios |
| 6,481,888 B1 | 11/2002 | Morgan |
| 6,895,618 B2 | 5/2005 | Jahrling |
| 7,103,932 B1 | 9/2006 | Kandora |
| 7,591,590 B2 | 9/2009 | Cadwalader |
| 7,663,128 B2 | 2/2010 | Arterson |
| 8,369,933 B2 | 2/2013 | Crisco |
| 2003/0167569 A1 | 9/2003 | Newkirk |
| 2004/0143177 A1 | 7/2004 | Falbo, Sr. |
| 2004/0216233 A1 | 11/2004 | Ludwig |
| 2005/0235421 A1 | 10/2005 | Ansel |
| 2006/0284123 A1 | 12/2006 | Goldstein |
| 2007/0029513 A1 | 2/2007 | Treuth |
| 2011/0184278 A1 | 7/2011 | Goff et al. |
| 2012/0132217 A1 | 5/2012 | Rees |
| 2012/0241652 A1 | 9/2012 | Jeschke |

FOREIGN PATENT DOCUMENTS

| | | |
|---|---|---|
| WO | 2012/121765 A1 | 9/2012 |
| WO | 2013/089608 A1 | 6/2013 |
| WO | 2014/028233 A1 | 2/2014 |
| WO | 2015/012906 A1 | 1/2015 |

RADIATION SHIELD ASSEMBLY

CROSS-REFERENCE TO RELATED APPLICATIONS

This utility patent application claims benefit of U.S. Provisional Application Ser. No. 62/087,282, filed Dec. 4, 2014, which is incorporated herein in its entirety by reference thereto.

BACKGROUND OF THE DISCLOSURE

During a fluoroscopy procedure a cardiologist will direct circulating staff such as a nurse to "push a drug" to a patient. An intravenous (IV) pole holding the necessary medications normally sits at the head of a table holding the patient. The nurse must approach the IV pole to administer the drugs and therefore may receive a very large dose of scatter radiation if the doctor is taking an X-Ray while the nurse is at the IV pole. This may happen because the doctor is focused on the patient and the procedure rather than on a location of the nurse. More specifically, if the physician's foot is on a fluoroscope pedal while the nurse is at the IV pole, the nurse will receive a high dose of scatter radiation during a normal X-ray (3-5 seconds fluoroscopy time). Aside from the potentially adverse impact on staff members' health, government regulations limit lifetime exposure to radiation. Thus, unnecessary exposures to scatter radiation can result in premature removal of experienced staff from fluoroscopy procedure rooms where they are most needed.

Moreover, equipment clutter in a procedure room can become a serious problem, especially during emergency procedures. Some equipment simply gets in the way of staff during crowded room emergency situations and is often pushed out of the way, even equipment intended for staff safety. Also, due to continual repositioning, the needed equipment is rarely in proper position when needed, so it commonly goes unused during an emergency.

A system that can be readily attached to, for instance, existing IV poles while allowing adequate space for other medical devices attached to a pole would be very useful and is urgently needed in fluoroscopy procedure rooms. The needed solution would provide a radiation shield near ionizing radiation sources to reduce radiation exposure to circulating staff, which would also allow a cardiologist to focus on a case rather than on staff location during fluoroscopy. Also, the needed solution would reduce equipment clutter and related inventory cost.

BRIEF SUMMARY OF THE DISCLOSURE

The inventors have unexpectedly discovered several modular radiation shielding systems useful in medical procedure rooms, particularly during fluoroscopy. Thus, the present disclosure is directed in general to these versatile, mobile, scatter radiation reduction systems.

According to one aspect of the present disclosure, a radiopaque system for use with medical equipment hangars may include a radiation shield having a first side and a second side and a radiopaque material interposed therebetween, the radiopaque material being at least 0.2 millimeters (mm) in thickness; and at least two attachment assemblies being asymmetrically disposed on the radiation shield, the attachment assemblies each being configured to adjustably connect the radiation shield to an equipment carrier, wherein the second side defines a face and the attachment assemblies depend from about two inches to about five inches from the face; wherein the radiation shield and the attachment assemblies are adapted to be coupled to one or more connection members of the equipment carrier.

In this aspect, the radiation shield may be rectilinear and rectangular in form, and the first side and the second side may include a weldable thermoplastic, which may be a polyethylene such as high density polyethylene. The radiopaque material may include lead, antimony, tin, barium, bismuth, cesium and/or tungsten. The lead, for instance, may be between about 0.2 mm to about 2 mm in thickness.

Also in this aspect, each of the attachment assemblies may conform to a shape of respective connection members of the equipment carrier. At least one of the connection members may be a rod or a limb.

Still further, the radiation shield may have a perimeter, and the attachment assemblies may be two or more clamps adapted to be coupled to one or more connection members of the equipment carrier. The clamps may be spaced apart from each other at divergent, different, or variable distances from the perimeter.

Also in this aspect, additional medical or other equipment may be located near the second side and set off from about two inches to about five inches from the face.

In this aspect, the system may also be adapted for vertical alignment on the equipment carrier in a first configuration and for inversion on the equipment carrier in a second configuration. Still further, the system may be adapted for substantially horizontal alignment on the equipment carrier in a third configuration.

In another aspect of the disclosure, a radiation shield assembly for use with medical equipment may include a radiation guard having a first face and a second face and a radiopaque material interposed therebetween, the radiopaque material being between about 0.2 mm to about 2 mm in thickness; and at least two connection assemblies operably disposed on the radiation guard, the connection assemblies being configured to adjustably connect the radiation guard to a medical device hangar, the radiation guard and the medical device hangar being spaced apart from each other; wherein at least one of the connection assemblies is adapted to be coupled to a connection member of the medical device hangar such that the radiation guard is in a configuration selected from the group consisting of a substantially vertical alignment on the medical device hangar, a substantially horizontal alignment on the medical device hangar, and an inverted position on the medical device hangar.

In this aspect, the first face and the second face may include thermoplastic material and the radiopaque material may be lead or another radiodense material. The radiation shield may be rectilinear and rectangular in form and define a perimeter. Two connection assemblies may be spaced apart from each other at different distances from opposite portions of the perimeter. The connection assemblies may be two or more clamps asymmetrically attached to the radiation shield at different distances from the perimeter.

Also in this aspect, the radiation guard and the medical device hangar may be spaced apart from each other from about two inches to about five inches such that the radiation guard does not interfere with equipment disposed on the medical device hangar.

In a further aspect of the disclosure, a radiopaque medical equipment system may include a mobile carrier; a radiopaque radiation shield having a first face and a second face, the radiopaque shield including radiodense material at least 0.2 mm in thickness to shield an operator from scatter radiation; and an attachment assembly disposed on the radiation shield, the attachment assembly connecting the radiation shield to the mobile carrier and depending from about two inches to about five inches from the second side.

In this aspect, the attachment assembly may be two connection assemblies asymmetrically attached to the radiation shield at different distances from a perimeter of the radiopaque radiation shield. The attachment assembly may be a press-fit, quick-release mechanism and/or a gravity hangar, both of which permit the radiopaque radiation shield to be easily removed from, or installed with, the mobile carrier.

The various embodiments described herein are non-limiting examples. Additional aspects of the present subject matter are set forth in, or will be apparent to, those of ordinary skill in the art from the detailed description herein. Modifications and variations to the specifically illustrated, referred and discussed features and elements hereof may be practiced in various embodiments; therefore, the disclosure is broader in scope than the described embodiments. Variations may include, but are not limited to, substitution of equivalent means, features, or steps for those illustrated, referenced, or discussed, and the functional, operational, or positional reversal of various parts, features, steps, or the like. Those of ordinary skill in the art will better appreciate the features and aspects of such variations upon review of the remainder of the specification.

BRIEF DESCRIPTION OF THE DRAWINGS

A full and enabling disclosure of the present subject matter, including the best mode thereof, directed to one of ordinary skill in the art, is set forth in the specification, which makes reference to the appended figures, in which.

DETAILED DESCRIPTION

Detailed reference will now be made to the drawings in which examples embodying the present subject matter are shown. The detailed description uses numerical and letter designations to refer to features of the drawings.

As required, detailed embodiments of the present disclosure are disclosed herein; however, it is to be understood that the disclosed embodiments are merely exemplary. The figures are not necessarily to scale, and some features may be exaggerated to show details of particular components. Therefore, specific structural and functional details disclosed herein are not to be interpreted as limiting, but merely as a basis for the claims and as a representative basis for teaching one skilled in the art to variously employ the embodiments and their equivalents disclosed herein.

It is an object of the present disclosure to overcome or ameliorate at least one of the disadvantages of the prior art, or to provide a useful alternative. Any discussion of the prior art in the specification should in no way be considered as an admission that such prior art is widely known or forms part of common general knowledge in the field.

In working environments for which the embodiments of the disclosure are intended, several components and related pieces of equipment may be used in conjunction with the disclosed embodiments. For instance, Cardio-TRAP® brand left radial access, right room operation, lower extremity peripheral platforms, such as those described in PCT application serial number PCT/US14/34788 may be used in intended environments of the present disclosure. The foregoing PCT patent application is hereby incorporated by reference herein in its entirety.

Figure 1:
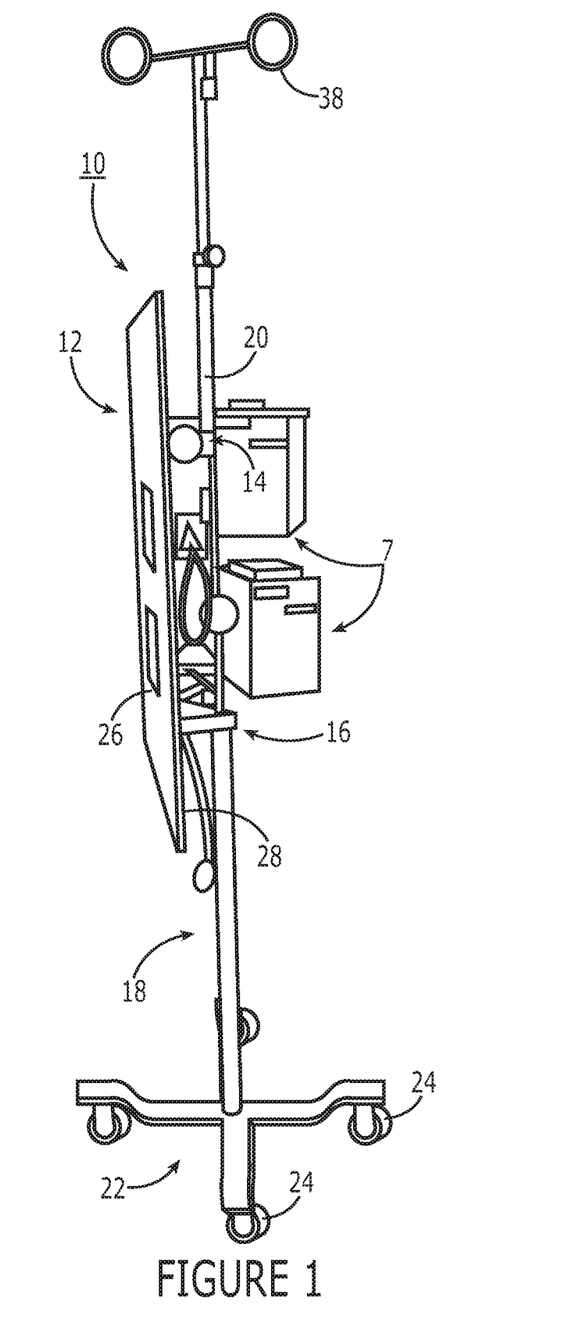
FIG. 1 is a side elevational view of a modular system according to an aspect of the disclosure.

Turning now to FIG. 1, according to an embodiment of the disclosure, a modular, radio-opaque, invertible shield system designated in general by the number 10 is shown. The radiation system 10 may broadly include a radiation shield, guard or planar member 12, a first mounting assembly 14, a second mounting assembly 16, and a medical device or equipment hangar 18. The hangar 18 may include a pole or rod 20, a base or stand 22, and one or more wheels 24. Alternatively, the hangar 18 can be an intravenous (IV) pole upon which the radiation shield 12 can be located, as explained below.

As FIG. 1 further shows, the shield 12 may have a first side or face 26 and an opposing second side or face 28. Here, one or both of the first and second mounting assemblies 14, 16 on face 28 may be connected, attached or mated to the rod 20 and/or to a catch, hook, loop or the like of the hangar 18, such as a connection member or receiver 38. As will be explained in detail below, the mounting assemblies 14, 16 may include screws, bolts with nuts, snaps, cord, quick-release mechanisms or other connection members for attaching or connecting the shield 12 to the hangar 18. Further, as described in greater detail below, the mounting assemblies 14, 16 may be set off from the pole 20 to accommodate other equipment 7 that may be on the hangar 18.

Figure 2:
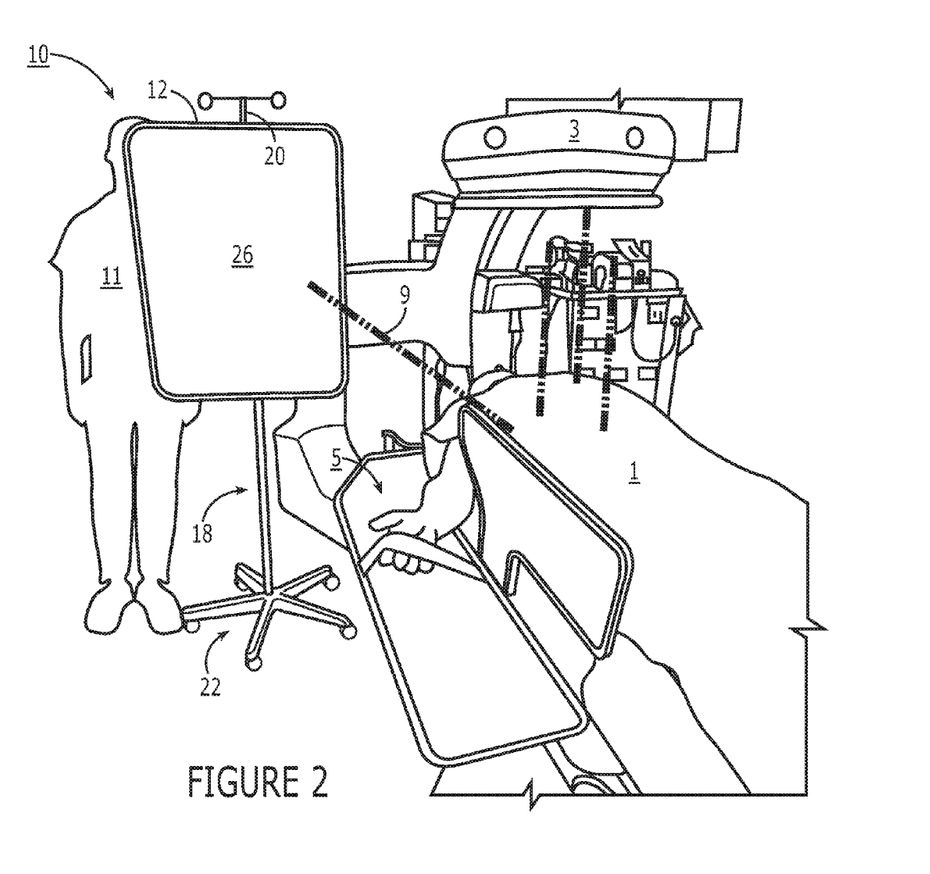
FIG. 2 is a front elevational view of the system as in FIG. 1 shown in an intended use environment.

FIG. 2 most clearly shows the face 26 of the shield 12. In this example, the system 10 is positioned near a patient 1 being imaged by a fluoroscopy machine 3 with a Cardio-TRAP® brand platform 5 serving to protect an attending cardiologist (not shown). More particularly, FIG. 2 shows that the shield 12 may be mated to the rod 20 of the hangar 18, which is positioned near the patient 1 using the mobile stand 22. A technician or nurse 11 may, for instance, stand behind the shield 12 to intravenously administer medications to the patient 1, or to monitor other equipment on the hangar 18. In this example, the shield 12 measures approximately 24 inches×32 inches and may be radiopaque or radiodense to block scatter radiation 9 being redirected or scattered from the patient 1. More specifically, the exemplary shield 12 blocks more than 90% of the scatter radiation 9 from reaching the staff member 11 positioned behind the shield 12 as discussed in additional detail with respect to FIG. 5 below.

Figure 3:
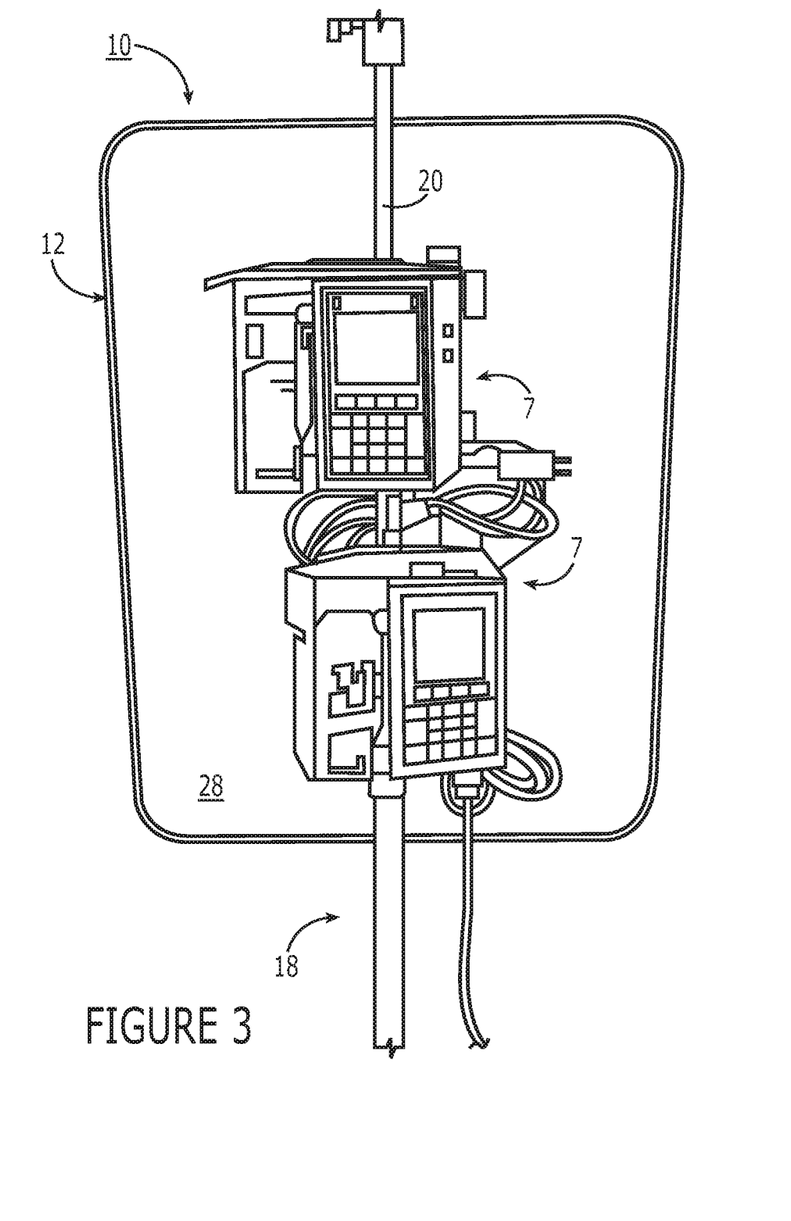
FIG. 3 is a partial, rear, elevational view of the system as in FIG. 1.

With reference now to FIG. 3, the face 28 of the shield 12 and the rod 20 of the hangar 18 are most clearly shown in a first, substantially vertical configuration. Also, as introduced above, the system 10 easily accommodates other equipment 7 that may be on the hangar 18. In other words, the shield 12 may be, for example, connected to the rod 20 without interfering with the preexisting equipment 7. Likewise, the shield 12 will not prevent attaching equipment 7 with the shield 12 in place first.

Figure 4:
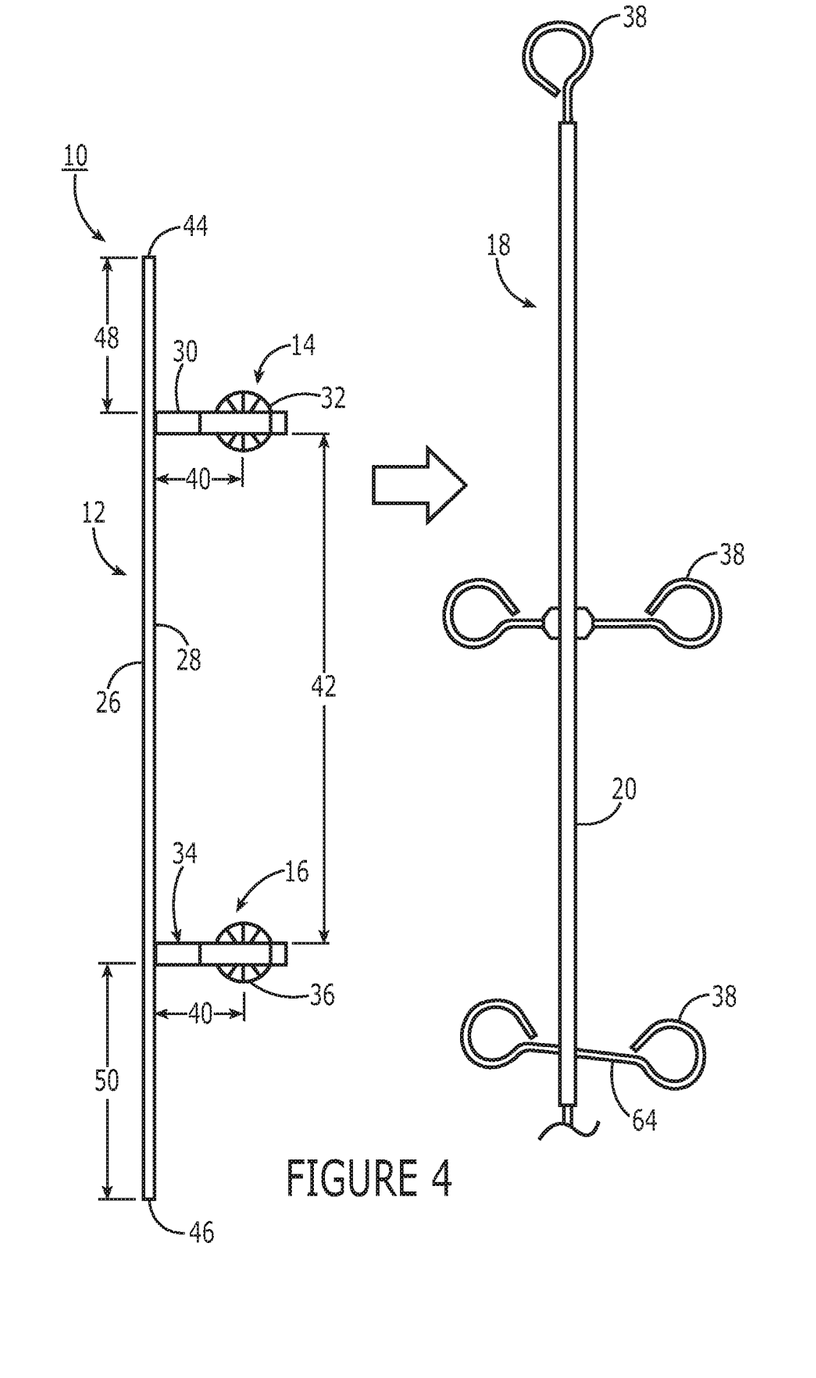
FIG. 4 is a schematic view of the system as in FIG. 1 shown being attached to a working component (partially shown)

In FIG. 4 the system 10 is shown schematically from one side being positioned for mating or connection with the rod 20 of the hangar 18 (partially shown for detail). As shown, the hangar 18 may have one or more receivers 38, each of which may have a rod or limb 64. The exemplary shield 12, as introduced, may have sides 26, 28 and be substantially planar in shape. The shield 12 may also have a top edge or side 44 and a bottom edge or side 46. Raised corners, for instance, may be provided at or on the edges 44, 46 such that the right radial base of the Cardio-TRAP® as described in application serial number PCT/US14/34788 may be hung on the shield 12 to prevent a hanging component from sliding off.

Also shown in the example of FIG. 4, the first mounting assembly 14 may include an extension component, arm or the like, such as bracket 30, and a closure or securement component, such as screw assembly 32. Likewise, the second mounting assembly 16 may include an extension component, arm or the like, such as bracket 34, and a closure or securement component, such as screw assembly 36. The mounting assemblies 14, 16 may be spaced from the face 28 approximately 2 inches to 5 inches as indicated by element number 40. This off-set 40 will provide space to accommodate other equipment that may be attached to the hangar 18. Although both mounting assemblies 14, 16 are shown with approximately equal off-sets 40, the disclosure is not limited to that arrangement. One of the assemblies could be off-set 2 inches and one could be off-set 5 inches to accommodate a particular hangar, for instance.

FIG. 4 further shows that mounting assembly 14 is spaced at a first distance 48 from edge 44 while mounting assembly 16 is spaced at a second distance 50 from edge 46. In this example, first distance 48 may be approximately 2 inches and second distance 50 may be approximately 4 inches. Thus, the shield 12 may be higher or lower relative to the hangar 18 depending on how the shield 12 is oriented or inverted in a second configuration. Here, the mounting assembly 14 is spaced apart at distance 42 from the mounting assembly 16. Distance 42 may be from 10 to 30 inches where the shield 12 may be about 36 inches in length and about 30 inches in width, although the shield 12 may be smaller or larger to accommodate specific user requirements, such as about 12 inches in length or about 10 inches in width. Furthermore, other mounting points or holes (not shown) may be provided and off-set by as much a six inches on an exemplary 24"×32" shield to permit greater adjustment.

Figure 5:
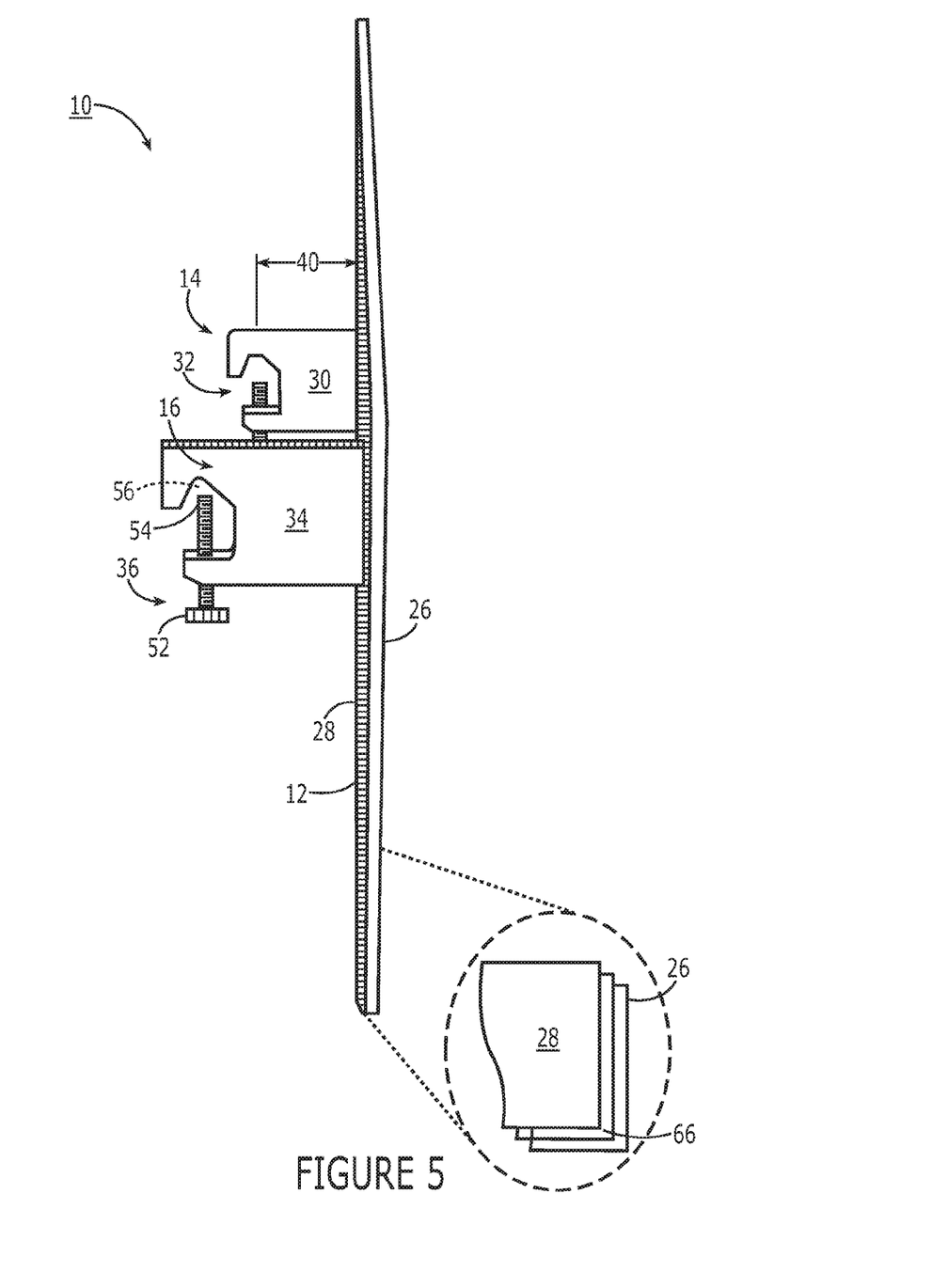
FIG. 5 is a perspective view of the system as in FIG. 4, including an exploded, partial inset view of an aspect of the disclosure.

With reference now to FIG. 5, the system 10 is shown in perspective and most clearly shows its mounting assemblies 14 and 16. In particular, the bracket 30 and a portion of the screw assembly 32 of mounting assembly 14 are shown. As introduced above, the screw assembly 32 is off-set from the face 28 of the shield 12 by the off-set 40. Similarly, the bracket 34 and the screw assembly 36 of mounting assembly 16 also are clearly shown in FIG. 5. The screw assembly 32 includes a grip or knurled knob 52 and a contact or closure end 54. The bracket 34 includes a gap or capture feature 56 to hold the rod 20 or the limb 64. Specifically, once the capture features 56 are positioned about respective rods 20 or limbs 64, the user may tighten or clamp the respective clamp assemblies 32, 36 to attach the radio-opaque guard 12 to the equipment hangar 18. In this example, the closure end 54 will press-fit against a portion of the rod 20 or limb 64 to press that portion into the capture feature 56 and render the system 10 stationary. To adjust or remove the shield 12, the user may loosen or unclamp the assemblies 32, 36.

FIG. 5 also shows in an exploded inset a partial view of the radio-opaque guard 12, which has radiodense material 66 heat-welded or pressure-welded between two sheets or pieces of approximately ⅛" thick high density polyethylene (HDPE), in this case, the sides 26, 28 of the shield 12. Embodiments including the material 66 to protect staff members from scatter radiation from a patient receiving fluoroscopy may weigh less than twelve pounds using approximately 0.5 millimeters (mm) of lead and up to approximately thirty pounds using up to 2 mm of lead. The material 66 may be lead, antimony, tin, barium, bismuth, cesium, tungsten, or any suitable radiodense material sufficient to absorb, reduce, inhibit, attenuate, or block ionizing radiation emanating from a patient being x-rayed.

Figure 6:
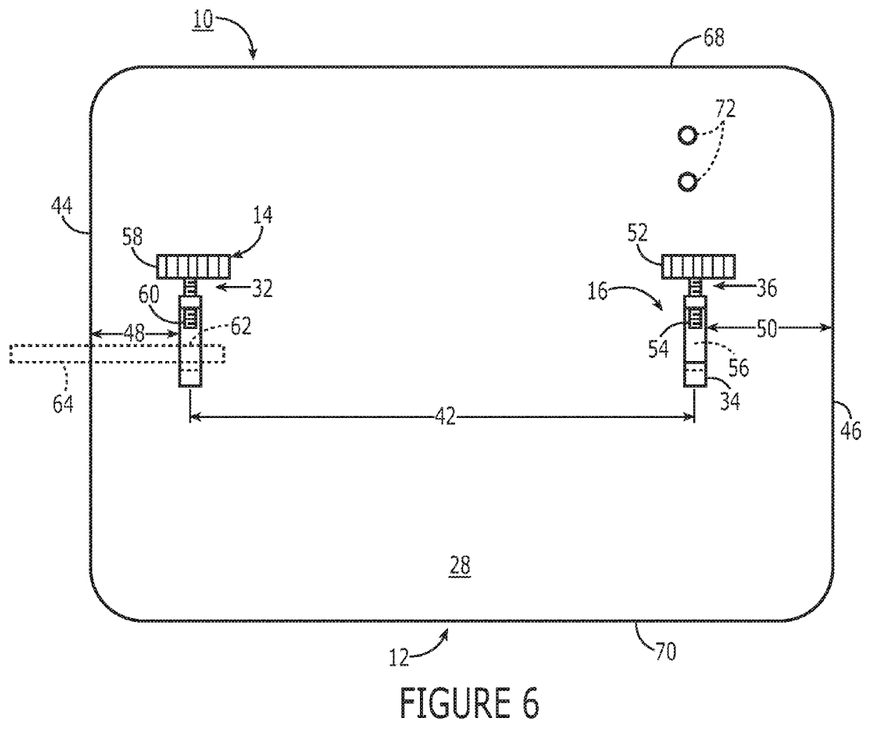
FIG. 6 is rear, elevational view of the system as in FIG. 5.

In FIG. 6, the system 10 is shown rotated 90 degrees in a third substantially horizontal configuration compared to, for instance, the first configuration or orientation of FIGS. 3 and 4. Here, sides or edges 44, 46, 68, 70 complete a perimeter of the shield 12. The mounting assemblies 14, 16 are spaced apart from each other on face 28 at the desired distance 42. The assembly 14 is at distance 48 from edge 44 and assembly 16 is at distance 50 from edge 46. In this example, the mounting assemblies 14, 16 are spaced asymmetrically from edges 44, 46 while spaced approximately equidistant from sides 68, 70. However, one or both of the mounting assemblies 14, 16, or an additional mounting assembly, could be attached to the shield 12 at, for instance, apertures 72.

FIG. 6 also most clearly shows knobs 52 and 58 of their respective clamp assemblies 36, 32. As shown, the clamp 36 includes the contact portion 54 and the clamp 32 includes contact portion 60. As introduced above, the limb 64 (in phantom for clarity) is captured, for example, between contact portion 60 and shoulder 62.

Figure 7:
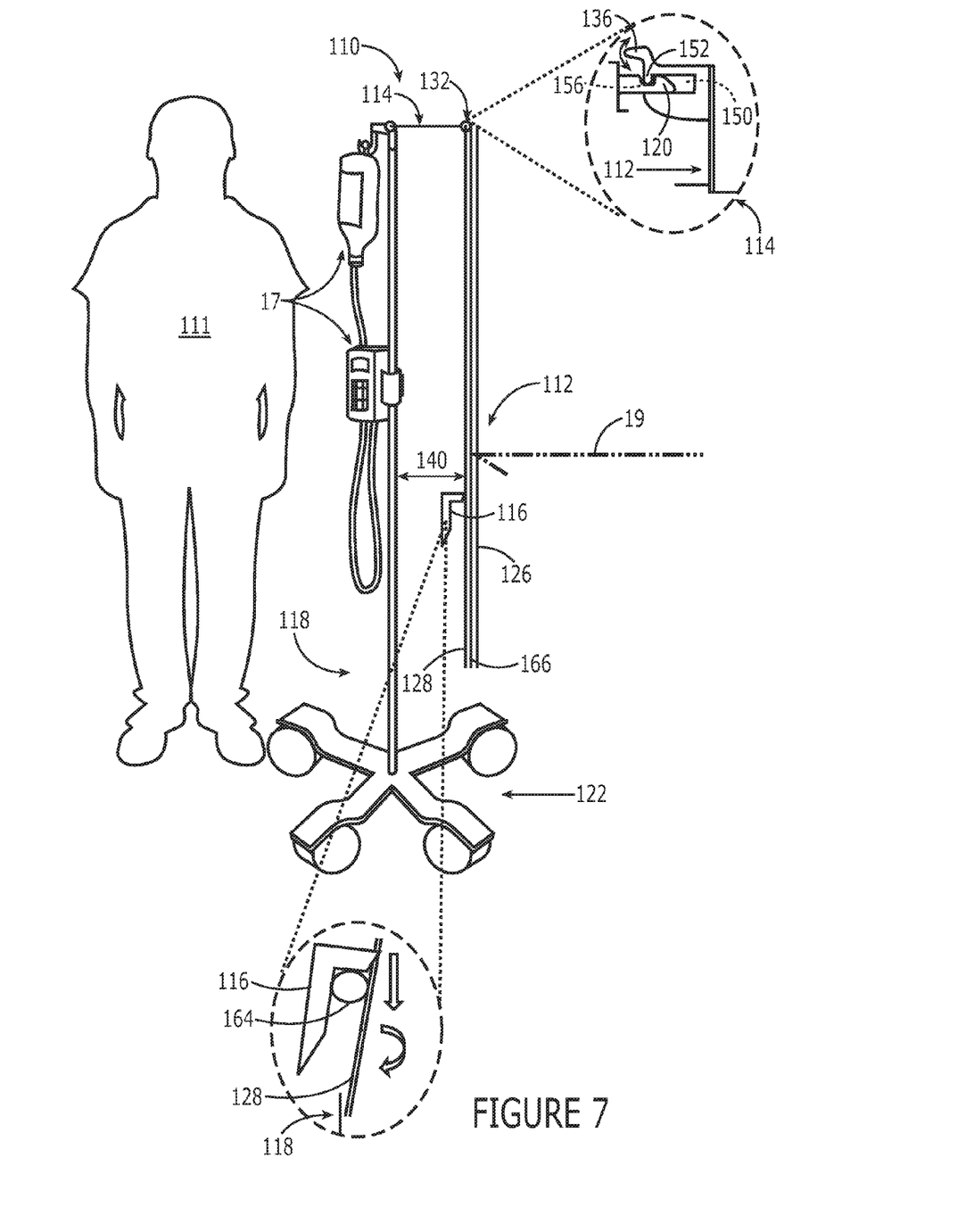
FIG. 7 is a perspective view of a radiodense system according to another aspect of the disclosure, including partial inset views of some features of the disclosure.

Turning to FIG. 7, another embodiment of a scatter radiation shielding system 110 includes a radiodense screen or shield 112, mounting assemblies 114 and 116 and a mobile stand or base 118 having wheels or rollers 122. The shield 112 may have sides 126, 128 or may be a unitary piece made of a radiopaque material. If separately included, as indicated by element number 166, the radiopaque material may include lead, antimony, tin, barium, bismuth, cesium, tungsten, or any suitable radiodense material sufficient to absorb, reduce, inhibit, attenuate, or block ionizing radiation—schematically shown and labeled element 19—from reaching a staff member 111 positioned behind the shield 112. The shield 112 may weigh between about twelve pounds to about thirty pounds and utilize approximately 0.5 mm to about 2 mm of radiopaque material 166.

As shown in detail in a first inset of FIG. 7, a quick-release assembly 132 may be located between the base 118 and the shield 112. Here, the assembly 132 is off-set by distance 140, which is at least the distance of a mounting assembly 116. As shown in a second inset, the mounting assembly 116 may be a gravity hangar wherein the shield 112 can be removed from the base 118 at assembly 132 and placed with or on another piece of equipment, or the assembly 116 can be used to further secure the shield 112 to the base 118 or to other components, and/or other components may be attached using the assembly 116. More particularly, the assembly 116 may be hung on a pole or rod 164, as shown in the inset, and the weight of the shield 112 will press down upon the pole 164 as indicated by the bold, downward facing arrow. The shield 112 may incline or tilt slightly, as indicated by the bold, curved arrow, until the face 128 contacts and stops at a portion of the base stand 118 (shown schematically in the inset for clarity).

In some embodiments, as further shown in FIG. 7, the distance 140 will be at least about 2 inches to about 6 inches, particularly 5 inches, to accommodate other equipment 17 on the stand 118. As briefly introduced above, the assembly 132, shown most clearly in the inset, may include a trigger or latch 136 and a channel or press-fit orifice 150 to receive a key or press-fit limb 120 from the assembly 114. The key 120 may have a receiver or notch 156, and the latch 136 may further include a protrusion, pin or catch 152 to nest in the receiver 156. Specifically, the radio-opaque guard 112 may be pressed onto the hangar 118 by pushing the key 120 and the latch 136 together. The latch 136 will have a spring constant to permit the pin 152 to be momentarily displaced in a first or stressed state, as indicated by the double-headed arrow, until the pin 152 centers on or aligns with the notch 156 and returns to a resting or second state in the notch 156. To adjust or remove the shield 112, a user may activate or pull on the latch 136, again as indicated by the double-headed arrow, to release the pin 152 from the notch 156. Those skilled in the art will understand that the assembly 132 can be arranged nearer the stand 118, that the key 120 and the latch 136 may be reversed, and/or that similar key and latch assemblies may be provided both nearer to the stand 118 and as shown in this example.

Detailed embodiments of the present disclosure have been described herein; however, it is to be understood that the disclosed embodiments are merely exemplary of the inventions herein that may be embodied in various forms. It will be appreciated that many modifications and other variations stand within the intended scope of this disclosure as claimed below. Furthermore, the foregoing description of various embodiments does not necessarily imply exclusion. For example, "some" embodiments may include all or part of "other" and "further" embodiments within the scope of this disclosure. In addition, "a" does not mean "one and only one;" "a" can mean "one and more than one." Furthermore "first", "second" and like terminology may be used herein as differentiating descriptors and may not mean primary, secondary and the like, nor do such terms dictate temporal limitations, unless expressly stated.

That which is claimed is:

1. A radiopaque system for use with medical equipment hangars, the radiopaque system comprising:
    a radiation shield having a first side and a second side and a radiopaque material interposed therebetween, the radiopaque material being at least 0.2 mm in thickness; and
    at least two attachment assemblies being asymmetrically disposed on the radiation shield, the attachment assemblies each being configured to adjustably connect the radiation shield to an equipment carrier, wherein the second side defines a face and the attachment assemblies depend from about two inches to about five inches from the face, wherein medical equipment is spaced apart from the radiation shield, the medical equipment being disposed proximate the face and the attachment assemblies;
    wherein the radiation shield and the attachment assemblies are adapted to be coupled to one or more connection members of the equipment carrier.

2. The system of claim 1, wherein the first side and the second side comprise a weldable thermoplastic.

3. The system of claim 2, wherein the thermoplastic comprises high density polyethylene.

4. The system of claim 1, wherein the radiopaque material is selected from the group consisting of lead, antimony, tin, barium, bismuth, cesium, tungsten, and combinations thereof.

5. The system of claim 4, wherein radiopaque material is between about 0.2 mm to about 2 mm in thickness.

6. The system of claim 1, wherein each of the attachment assemblies substantially conform to a shape of respective connection members of the equipment carrier.

7. The system of claim 1, wherein at least one of the connection members is a rod or a limb.

8. The system of claim 1, wherein the radiation shield defines a perimeter and the attachment assemblies are at least two clamps adapted to be coupled to one or more connection members of the equipment carrier, the two clamps being spaced apart from each other at divergent distances from the perimeter, the clamps being disposed at an off-set on the radiation shield.

9. The system of claim 1, wherein the medical equipment disposed proximate the face depends in a direction away from the face with a rod being disposed between the face and the medical equipment.

10. The system of claim 9, wherein the medical equipment is set off from about two inches to about five inches from the face.

11. The system of claim 1, wherein the radiation shield has a substantially rectilinear form.

12. The system of claim 1, wherein the radiation shield has a substantially rectangular form.

13. The system of claim 1, wherein the system is adapted for substantially vertical alignment on the equipment carrier in a first configuration.

14. The system of claim 1, wherein the system is adapted for inversion on the equipment carrier in a second configuration.

15. The system of claim 1, wherein the system is adapted for substantially horizontal alignment on the equipment carrier in a third configuration.

16. A radiation shield assembly for use with medical equipment, the radiation shield assembly comprising:
    a radiation guard having a first face and a second face and a radiopaque material interposed therebetween, the radiopaque material being between about 0.2 mm to about 2 mm in thickness; and
    at least two connection assemblies operably disposed on the radiation guard, the connection assemblies being configured to adjustably connect the radiation guard to a medical device hangar, the radiation guard and the medical device hangar being spaced apart from each other;
    wherein at least one of the connection assemblies is adapted to be coupled to a connection member of the medical device hangar such that the radiation guard is in a configuration selected from the group consisting of a substantially vertical alignment on the medical device hangar, a substantially horizontal alignment on the medical device hangar, and an inverted position on the medical device hangar.

17. The system of claim 16, wherein the first face and the second face comprise thermoplastic material and the radiopaque material comprises lead.

18. The system of claim 16, wherein the radiation shield is substantially rectilinear and rectangular in form and defines a perimeter, the two connection assemblies being spaced apart from each other at different distances from opposite portions of the perimeter.

19. The system of claim 16, wherein the connection assemblies are two clamps asymmetrically attached to the radiation shield at different distances from the perimeter thereby defining an off-set on the radiation shield.

20. The system of claim 16, wherein the radiation guard and the medical device hangar are spaced apart from each other from about two inches to about five inches such that the radiation guard does not interfere with equipment disposed on the medical device hangar.

21. A radiopaque medical equipment system, comprising:
a mobile carrier;
a radiopaque radiation shield having a first face and a second face, the radiopaque shield including radiodense material being at least 0.2 mm in thickness to shield an operator from scatter radiation; and
an attachment assembly disposed on the radiation shield, the attachment assembly being configured to connect the radiation shield to the mobile carrier and depending at least about two inches from the second face, wherein a plurality of medical equipment can be disposed proximate the second face and the attachment assembly, a rod being disposed between the second face and the medical equipment.

22. The radiopaque medical equipment system of claim 21, wherein the attachment assembly further comprises two connection assemblies asymmetrically attached to the radiation shield at different distances from a perimeter of the radiopaque radiation shield, the two connection assemblies being offset from each other and at unequal distances on the radiopaque radiation shield.

23. The radiopaque medical equipment system of claim 21, wherein the attachment assembly is a press-fit, quick-release mechanism.

24. The radiopaque medical equipment system of claim 21, wherein the attachment assembly is a gravity hangar.

25. The radiopaque medical equipment system of claim 24, wherein the radiopaque radiation shield is adapted for removal from the mobile carrier.

* * * * *